United States Patent [19]

Ogle

[11] 4,296,747
[45] Oct. 27, 1981

[54] CATH-A-JET

[75] Inventor: Robert W. Ogle, Newport Beach, Calif.

[73] Assignee: IMS Limited, El Monte, Calif.

[21] Appl. No.: 120,532

[22] Filed: Feb. 11, 1980

[51] Int. Cl.³ .............................................. A61M 5/00
[52] U.S. Cl. ................................. 128/220; 128/214 R
[58] Field of Search ............... 128/249, 220, 221, 349, 128/214 R

[56] References Cited

U.S. PATENT DOCUMENTS

| | | | |
|---|---|---|---|
| 1,367,008 | 2/1921 | Bessesen | 128/220 |
| 2,490,553 | 12/1949 | Smith | 128/220 |
| 2,495,026 | 1/1950 | Smith | 128/220 |
| 2,568,346 | 9/1951 | Lockhart | 128/220 |
| 3,890,972 | 6/1975 | Standley et al. | 128/220 |
| 3,941,131 | 3/1976 | Ogle | 128/220 |
| 4,196,731 | 4/1980 | Laurin et al. | 128/214 R |

Primary Examiner—Gene Mancene
Assistant Examiner—Wenceslao J. Contreras
Attorney, Agent, or Firm—Joseph E. Mueth

[57] ABSTRACT

A device for introducing fluid into urethral catheters having a free end fitment and/or a pierceable injection site comprising a syringe structure actuable to expel fluid from an outlet at one end thereof, and a connector structure extending from the one end of the syringe structure and defining an axial fluid passage communicating with the outlet. The connector structure is provided with a first axially tapered surface portion receivable in sealing relationship within the free end fitments of urethral catheters, and a second axially tapered surface portion engageable in sealing relationship with a luer needle fitment. Fluid from the syringe structure is introduced into the catheters either through a free end fitment or an injection site for passage toward the urethra.

5 Claims, 8 Drawing Figures

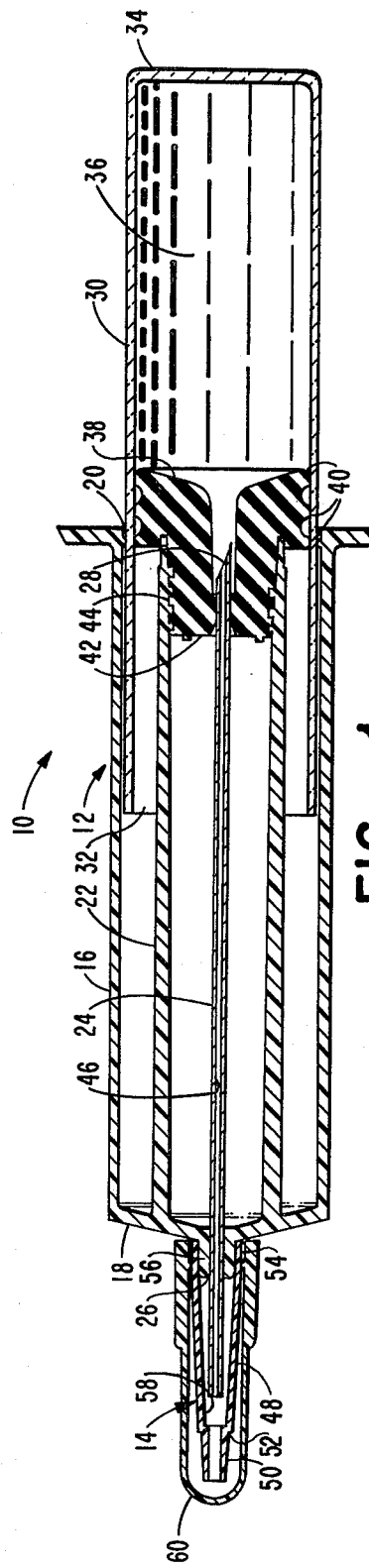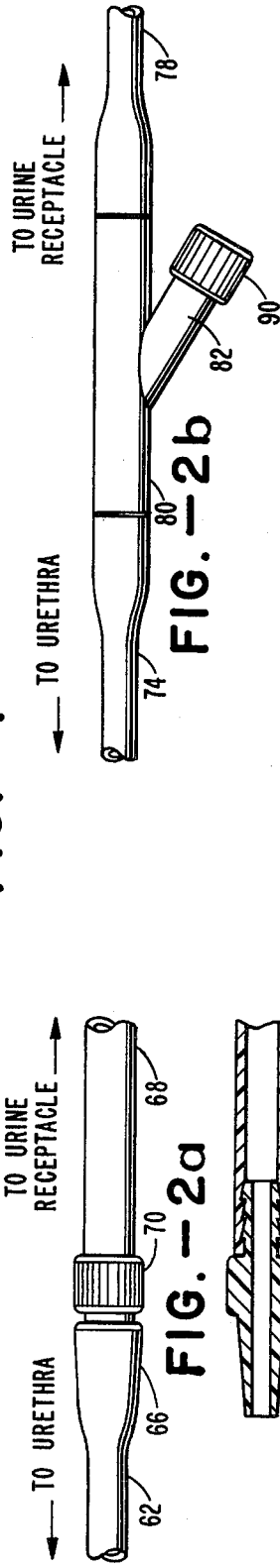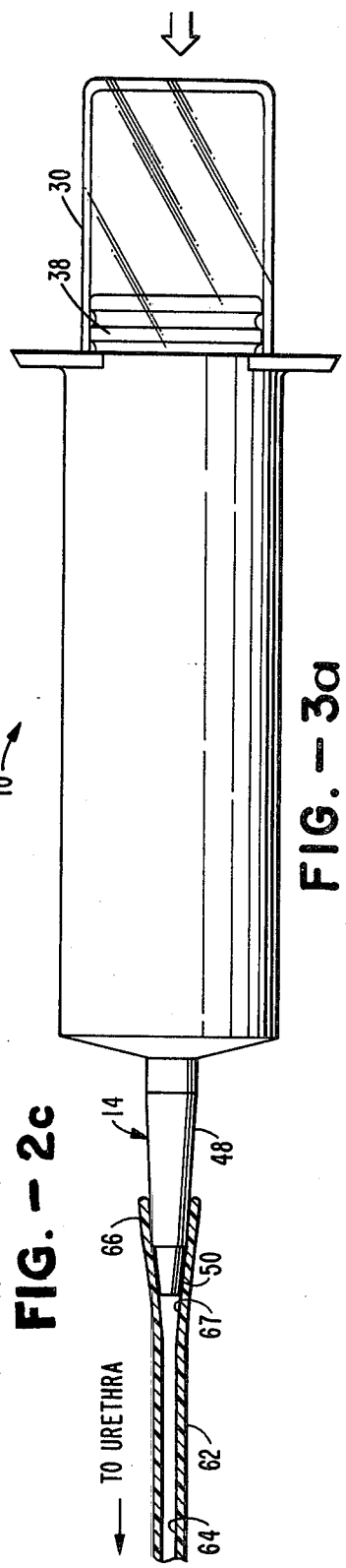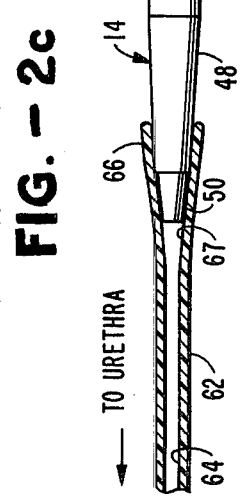

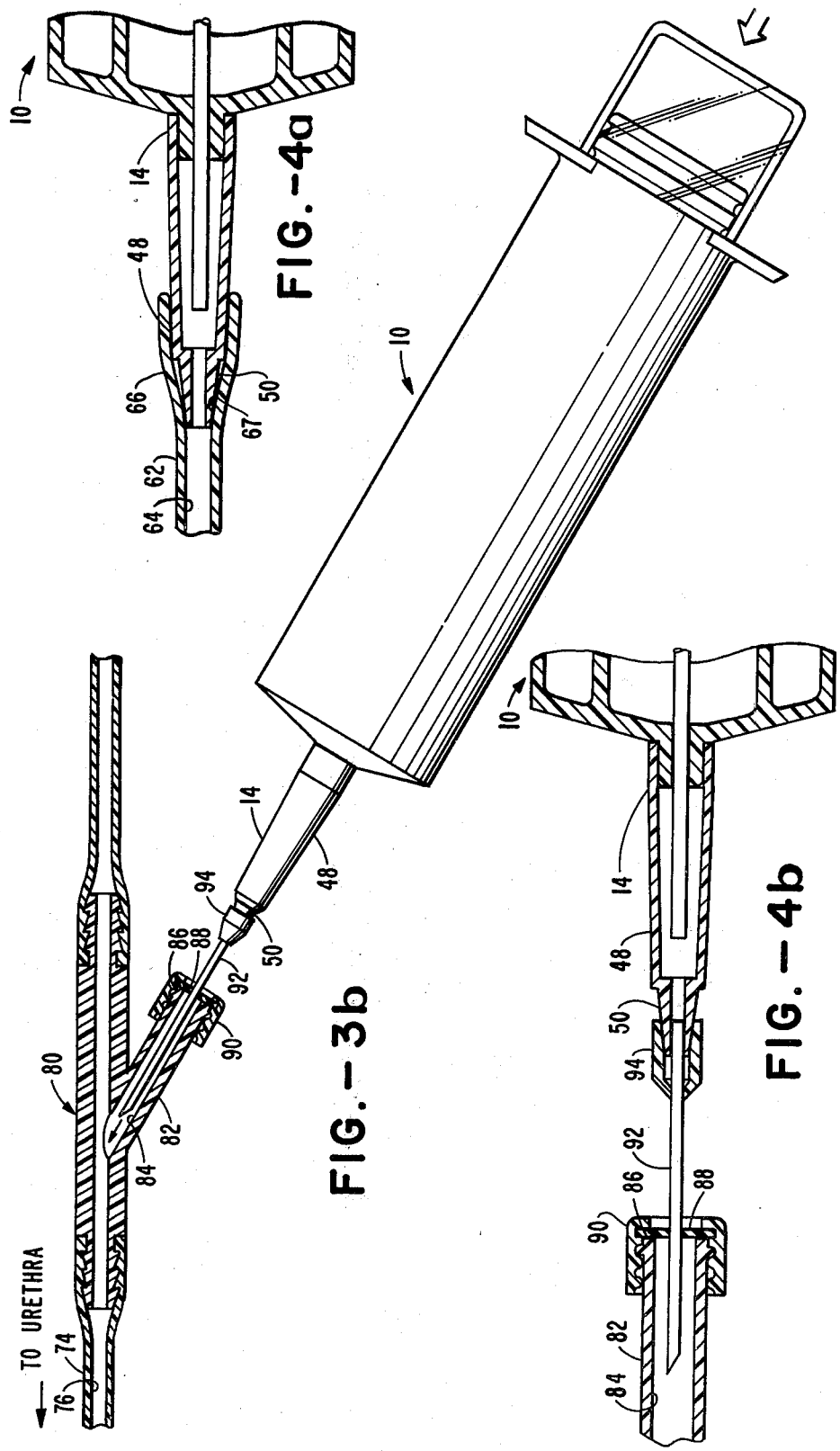

CATH-A-JET

BACKGROUND OF THE INVENTION

This invention relates to the Foley catheter art, and more particularly to an improved device for the introduction of cleansing or irrigating fluid into Foley catheters for passage toward the human urethra.

In the practice of medicine, catheters have long been used to drain urine from the bladders of patients who are unable to control the discharge of urine due to medication or physical incapacity. Catheters of this type, known in the trade as Foley catheters, are introduced through the human urethra to the bladder, at which point they are provided with an inflatable portion which maintains the catheter in position against the fluid pressure within the bladder. It has been found that the fine cannular opening within Foley catheters tends to become clogged during use from a build-up of calcium and other elements of the urine. It is then desirable to pass a cleansing fluid, such as acetic acid, through the catheter for the purpose of restoring it to an unclogged condition. It is also desirable in many cases to irrigate an infected or otherwise unhealthy bladder of a patient carrying a Foley catheter. This is, of course, most effectively done through the catheter itself.

The cleansing and irrigating procedures noted above have heretofore been accomplished with conventional needle-type syringes. To aid in these procedures, one type of commercially available Foley catheter is provided with an injection site having a pierceable diaphragm through which a cleansing or irrigating fluid can be introduced. Many other urethral catheters of the Foley type have no injection site, but are provided either with a tapered or a cylindrical free end fitment which is releasably connected to a discharge tube running to a urine bag or other receptacle. To my knowledge, the flushing or irrigating procedures are commonly performed on these catheters by disconnecting the waste conduit from the free end fitment, and expelling the fluid from a needle-type syringe into the free end. A substantial amount of the cleansing or irrigating fluid may be lost in this operation, and it is difficult to establish sufficient fluid pressure to force the fluid through the length of the catheter.

Therefore, in many applications it is desirable to provide a device able to effectively pass a cleansing or irrigating fluid through the entire length of urethral catheters of any conventional construction. It is particularly desirable to provide a device able to engage the free end fitments of urethral catheters as well as imperforate injection sites.

SUMMARY OF THE INVENTION

Briefly, the present invention comprises a device for introducing fluid into catheters of the type which are partially receivable in the human urethra to drain urine from the bladder and have a free end fitment and/or a pierceable injection site, comprising: syringe means actuable to expel fluid from an outlet at one end thereof; connector means extending from the one end of the syringe means and defining an axial fluid passage communicating with the outlet; a first axially tapered surface portion of the connector means receivable in sealing relationship with the free end fitments of urethral catheters; and a second axially tapered surface portion of the connector means engageable in sealing relationship with a luer needle fitment; whereby fluid can be introduced into urethral catheters either through a free end fitment or an injection site for passage toward the human urethra. The second tapered surface portion may be smaller in diameter than the first tapered surface portion and may be positioned outwardly thereof. The syringe means may comprise a cylindrical vial having an open end and a closed end, a resilient plug adapted to be inserted at least partially through the open end of the vial; a plurality of outwardly extending rings upon the plug engaging the walls of the wall with a press fit; a cylindrical member having one closed end with an outlet therein, the cylindrical member being adapted to hold a needle communicating with the outlet and extending inwardly into the cylindrical member and having a sharpened inner end; and interlocking means on the cylindrical member and cooperating interlocking means on the plug, whereby upon interlocking of the plug with the cylindrical member the vial is first held in an assembled but non-operating position and upon further interlocking of the plug with the cylindrical member, the plug is adapted to be pierced by the needle and the needle communicated with the vial without the application of substantial axial pressure on the plug and the plug is locked securely to the cylindrical member to permit expulsion of the contents of the vial through the outlet upon exertion of pressure on the vial.

It is an object of the present invention to provide a simple and economical device able to introduce a fluid into any urethral catheter having either a free end fitment or a pierceable injection site.

It is another object of the present invention to provide a device engageable with the free end fitment of a Foley catheter to introduce a cleansing or irrigating fluid through the length of the catheter.

The connector means of the present invention overcome the problems heretofore experienced by provision of a pair of co-axial differently tapered surface portions engageable with free end fitments of urethral catheters and luer needle fitments, respectively. The first surface portion is tapered to fit into both tapered and cylindrical free end fitments of urethral catheters and exhibit optimum sealing characteristics therewith. For this purpose, the taper of the first surface portion is different from and preferably greater than the taper of the free end fitments, producing a very effective seal when the respective elements interfit.

While the luer taper of the second surface portion is well known in the art for engagement with releasable luer needle fitments, the use of such a tapered surface portion in combination with another surface portion extending from the outlet of a syringe is novel and highly advantageous. The resulting device can be used to introduce a cleansing or irrigating fluid into urethral catheters having either free end fitments or pierceable injection sites, or both. The first and second tapered surface portions are axially aligned with the outlet of a syringe, and are joined by a transition portion forming a step from the smallest diameter of the first surface portion to the largest diameter of the second surface portion. When the device of the present invention is used, the presence of an additional tapered surface portion which is not necessary to the particular procedure being performed does not interfere in any way with the operation of the device. In the "closed technique" wherein a luer needle is fitted to the second tapered surface portion and an injection site on the catheter is pierced by the needle, the existence of the first tapered surface portion serves only to displace the syringe rearwardly a distance equal to the length of the first surface portion. In the "open technique" wherein the first tapered surface portion is received within the free end fitment of a catheter, the relatively short and narrow second surface portion merely extends a small distance further into the fitment.

BRIEF DESCRIPTION OF THE DRAWINGS

The above and other objects of the present invention may be more fully understood from the following detailed description taken together with the accompanying drawings wherein similar reference characters refer to similar elements throughout, and in which:

FIG. 1 is a vertical sectional view of the device constructed according to the present invention;

FIGS. 2a and 2b represent portions of two different commercially available urethral catheter assemblies;

FIG. 2c is a sectioned view of a portion of the structure of FIG. 2a;

FIG. 3a is a partial sectional view showing the device of FIG. 1 in use relative to the catheter of FIG. 2a;

FIG. 3b is a partial sectional view showing the device of FIG. 1 in use relative to the catheter of FIG. 2b;

FIG. 4a is a fragmentary enlarged sectional view showing the engagement of the device of FIG. 1 with the catheter of FIG. 2a; and FIG. 4b is an enlarged sectional view showing the engagement of the device of FIG. 1 with the catheter of FIG. 2b.

DESCRIPTION OF THE PREFERRED EMBODIMENTS

Referring now to the drawings, there is illustrated, in FIG. 1 thereof, a device constructed according to the present invention, generally designated 10. The device 10 includes a syringe assembly 12 carrying a connector element 14 at one end thereof.

The syringe assembly 12 comprises a housing 16 having an end wall 18 and an open end 20. A cylindrical member 22 carried by the end wall 18 is located within the housing 16 and is co-axial therewith. A hollow needle 24 extends through an outlet 26 in the end wall 18 and extends inwardly into the cylindrical member 22 to a sharpened inner end 28. A cylindrical vial 30 having an open end 32 and a closed end 34 is filled with a cleansing or irrigating fluid 36 and closed with a resilient plug 38 adapted to be inserted at least partially through the open end 32. The resilient plug 38 is provided with a plurality of outwardly extending rings 40 engaging the walls of the vial to produce an effective seal therewith.

The plug 38 is initially imperforate and is provided with an outwardly extendng threaded projection 42 engageable with internal threads 44 of the cylindrical member 22. The plug 38 may thus be interlocked with the cylindrical member 22 and advanced therealong in the direction of the end wall 18 by rotation of the vial 30 and the plug 38. This advancement of the plug 38 causes the stationary needle 24 to pierce the plug, communicating the cannula 46 of the needle with the interior of the vial. This is the condition illustrated in FIG. 1. Axial pressure applied to the vial 30 then pressurizes the fluid 36 contained therein and forces the fluid from the vial along the cannula 46.

The connector element 14 is provided with first and second co-axial portions 48 and 50, respectively, joined by an essentially radial transition portion 52 forming a step between the smaller end of the portion 48 and the larger end of the portion 50. A short cylindrical collar 54 at the larger end of the portion 48 is received over and bonded to an annular hub 56 about the outlet 26. The first and second portions 48 and 50 are each tapered, and together form an axial passage 58 communicating with the cannula 46 of the syringe assembly 12. The second portion 50 is provided with a luer taper for engagement with injection needles having conventional luer fitments, and the larger diameter portion 48 is tapered as discussed hereinbelow. While the portions 48 and 50 are preferably given different angles of taper as well as different diameters due to the different purposes for which they are used, satisfactory results are obtainable with a connector element 14 in which the portions 48 and 50 have the same angle of taper but are of different diameters. A cover 60 engaging the short cylindrical collar 54 may enclose the entire connector element 14 and seal it from contamination prior to use.

FIGS. 2a and 2b illustrate the connecting portions of the two predominant forms of urethral catheters. The structure and operation of such catheters and the waste systems attached thereto are well known in the medical field and will not be discussed in detail herein. The portions shown are those which are acted upon directly by the device 10 and are therefore necessary to an understanding of the operation of the device.

The catheter portion shown in FIG. 2a is also shown in FIGS. 2c, 3a and 4a, in conjunction with the device 10. A catheter 62 having a fine cannular passage 64 is provided at its free end with a fitment 66 which is flared outwardly to form a tapered interior surface 67. A waste line 68 is connected to the free end fitment 66 of the catheter 62 through a connector 70 carried by the line 68. The connector 70 is provided with a tapered exterior surface 72 receivable within the free end fitment 66 to seal against the tapered surface 67. A releasable connection is thus provided between the waste line 68 and the catheter 62.

The tapered portion 48 of the connector element 14 is also receivable within the fitment 66 in a sealing relationship. The taper of the portion 48 is preferably somewhat greater than that of the interior surface 67 to enable an effective but easily releasable seat to be formed between the element 14 and the fitment 66. The application of axial pressure to the vial 30 of the device 10 when the element 14 is engaged with the fitment 66 causes the fluid 36 within the vial to be forced through the cannular passage 64 toward the patient's bladder. This cleanses or flushes the passage 64 as it provides irrigation to the patient's bladder.

In operation, the connector 70 is disengaged from the free end fitment 66 whenever the cannular passage 64 becomes clogged or it is desired to irrigate the bladder of the patient. The connector element 14 is then pressed into the fitment 66 to provide the desired seal, and the fluid 36 is administered by depressing the vial 30. After administration of the fluid 36, the device 10 is easily removed from the catheter 62 and the connector 70 is reinserted into the fitment 66 to allow the patient to pass the fluid 36 and any dissolved calcium or other materials to a urine bag or other receptacle (not shown). This technique thus requires that the catheter assembly be opened before flushing or irrigation can take place; however, it is highly advantageous because it enables the fluid 36 to be forced along the catheter 62 in the direction of the patient's bladder to maximize the flushing or cleansing action and provide the greatest amount of irrigation to the bladder.

The catheter of FIG. 2b is shown in conjunction with the device 10 in FIGS. 3b and 4b. A catheter tube 74 having a fine cannular passage 76 is connected to a waste line 78 by a "Y" fitting 80 having a branch 82 forming an injection site. A passage 84 within the branch 82 terminates at an outer end 86 sealed by an imperforate diaphragm 88 held in place by a threaded annular cap 90.

When it is desired to introduce the fluid 36 for flushing or irrigation purposes, the introduction is accomplished by injection of the fluid through the diaphragm 88 with a needle. FIGS. 3b and 4b illustrate the device 10 having a hollow needle 92 fixed to the connector element 14 by engagement of a luer needle fitment 94 with the luer-tapered portion 50. The needle 92 may thus be made to penetrate the diaphragm 88 when it is desired to introduce cleansing or irrigating fluid into the catheter tube 74. This is accomplished with the catheter otherwise remaining entirely closed and functioning. After the desired fluid is introduced, the needle 92 is withdrawn from the diaphragm 88 to allow the diaphragm to reseal itself.

It will be understood that the structure disclosed for the syringe assembly 12 is merely illustrative, and any syringe capable of expelling a fluid from an opening therein will function satisfactorily in the device 10. The materials used for the various elements of the present invention are likewise subject to wide variation.

The fluid 36 introduced into the urethral tract by the device 10 is most commonly acetic acid; however, other medicaments can be added to or substituted for acetic acid to treat infections or other adverse conditions of the bladder.

It can therefore be seen that there has been provided an improved device for introducing fluids into urethral catheters which is operable in conjunction with catheters having a free end fitment and/or a pierceable injection site. Depending upon the type of catheter being used, the device of the present invention will function according to both the open and the closed techniques described above.

The appended claims are intended to cover all variations and adaptations falling within the true scope and spirit of the present invention.

I claim:

1. A device for introducing fluid into catheters of the type which are partially receivable in the human urethra to drain urine from the bladder and have a free end fitment and/or a pierceable injection site, comprising:

syringe means actuable to expel fluid from an outlet at one end thereof;
   connector means extending from said one end of the syringe means and defining an axial fluid passage communicating with said outlet;
   a first axially tapered surface portion of the connector means receivable in sealing relationship within the free end fitments of urethral catheters;
   a second axially tapered surface portion of the connector means engageable in sealing relationship with a luer needle fitment;
   said second tapered surface portion being smaller in diameter than and positioned outwardly of said first tapered surface portion; and
   a transition surface portion between the first and second tapered surface portions, said transition surface portion comprising a step in the diameter of the connector means.
   whereby fluid can be introduced into urethral catheters either through a free end fitment or an injection site for passage toward the human urethra.

2. The device recited in claim 1 wherein said second surface portion is tapered at a greater angle than said first surface portion.

3. The device recited in claim 1 which includes a removable cover on said connector means for maintaining the connector means in a sterile condition prior to use.

4. The device recited in claim 1 which includes an injection needle having on one end a luer fitment engageable with said second tapered surface portion.

5. The device recited in claim 1 wherein said syringe means comprises a cylindrical vial having an open end and a closed end, a resilient plug adapted to be inserted at least partially through said open end of said vial; a plurality of outwardly extending rings upon said plug engaging the walls of said vial with a press fit; a cylindrical member having one closed end with an outlet therein, said cylindrical member being adapted to hold a needle communicating with said outlet and extending inwardly into said cylindrical member and having a sharpened inner end; and interlocking means on said cylindrical member and cooperating interlocking means on said plug, whereby upon interlocking of said plug with said cylindrical member said vial is first held in an assembled but non-operating position and upon further interlocking of said plug with said cylindrical member, said plug is adapted to be pierced by said needle and said needle communicated with said vial without the application of substantial axial pressure on said plug and said plug is locked securely to said cylindrical member to permit expulsion of the contents of said vial through said outlet upon exertion of pressure on said vial.

* * * * *